US012758475B2

(12) United States Patent
Schultz

(10) Patent No.: US 12,758,475 B2
(45) Date of Patent: Oct. 13, 2026

(54) BALANCED DENTAL CARE COMPOSITIONS AND METHODS

(71) Applicant: Anthony Leon Schultz, Boise, ID (US)

(72) Inventor: Anthony Leon Schultz, Boise, ID (US)

( * ) Notice: Subject to any disclaimer, the term of this patent is extended or adjusted under 35 U.S.C. 154(b) by 88 days.

(21) Appl. No.: 18/933,997

(22) Filed: Oct. 31, 2024

(65) Prior Publication Data

US 2025/0143987 A1 May 8, 2025

Related U.S. Application Data

(60) Provisional application No. 63/547,837, filed on Nov. 8, 2023.

(51) Int. Cl.

| | |
|---|---|
| ***A61K 8/34*** | (2006.01) |
| ***A61K 8/20*** | (2006.01) |
| ***A61K 8/24*** | (2006.01) |
| ***A61K 8/25*** | (2006.01) |
| ***A61K 8/368*** | (2006.01) |
| ***A61K 8/42*** | (2006.01) |
| ***A61K 8/46*** | (2006.01) |
| ***A61K 8/73*** | (2006.01) |
| ***A61K 8/92*** | (2006.01) |
| ***A61K 8/9789*** | (2017.01) |
| ***A61K 31/00*** | (2006.01) |
| ***A61K 33/18*** | (2006.01) |

(52) U.S. Cl.

CPC ................ *A61K 8/347* (2013.01); *A61K 8/20* (2013.01); *A61K 8/24* (2013.01); *A61K 8/25* (2013.01); *A61K 8/345* (2013.01); *A61K 8/368* (2013.01); *A61K 8/42* (2013.01); *A61K 8/463* (2013.01); *A61K 8/731* (2013.01); *A61K 8/927* (2013.01); *A61K 8/9789* (2017.08); *A61K 31/658* (2023.05); *A61K 33/18* (2013.01)

(58) Field of Classification Search

CPC ...... A61K 47/38; A61K 8/0216; A61K 8/042; A61K 8/345; A61K 8/355; A61K 8/731; A61K 9/006; A61K 9/06; A61K 31/122; A61K 31/785; A61K 33/18; A61K 33/38; A61K 38/1793; A61K 38/18; A61K 38/1858; A61K 38/40; A61K 39/3955; A61K 47/10; A61K 6/35; A61K 2039/505; A61K 2800/10; A61K 2800/31; A61K 2800/92; A61Q 11/00

See application file for complete search history.

(56) References Cited

U.S. PATENT DOCUMENTS

| | | | |
|---|---|---|---|
| 8,029,812 B2 | 10/2011 | Sunkara | |
| 2007/0292360 A1* | 12/2007 | Siegel | A61K 8/362 424/53 |
| 2017/0172977 A1 | 6/2017 | Kleidon et al. | |
| 2018/0168955 A1* | 6/2018 | Shabo | A61K 8/20 |
| 2020/0330339 A1 | 10/2020 | Anastassov et al. | |
| 2021/0244653 A1* | 8/2021 | Mainella | A61K 8/676 |
| 2021/0275436 A1 | 9/2021 | Nam et al. | |
| 2022/0023022 A1 | 1/2022 | Ehrenpreis et al. | |

FOREIGN PATENT DOCUMENTS

| | | |
|---|---|---|
| CA | 3152782 A1 | 3/2021 |
| CA | 3150914 A1 | 4/2021 |
| WO | WO2021071867 | 4/2021 |
| WO | WO2021072422 | 4/2021 |
| WO | WO2021072423 | 4/2021 |

OTHER PUBLICATIONS

Hatch-McChesney et al., "Iodine and Iodine Deficiency: A Comprehensive Review of a Re-Emerging Issue," Nutrients 2022 vol. 14, No. 3474, https://doi.org/10.3390/nu14173474, Aug. 24, 2022, 11 pages.

Buzalaf et al., "Protective effect of calcium silicate toothpaste on enamel erosion and abrasion in vitro," Heliyon, Apr. 14, 2021;7(4):e06741. doi: 10.1016/j.heliyon.2021.e06741. eCollection Apr. 2021, 5 pages.

"Is CBD a Depressant or Stimulant," [accessed Sep. 26, 2024] [ available online at <https://cfah.org/is-cbd-depressant-or-stimulant/ >], 10 pages.

* cited by examiner

*Primary Examiner* — Lezah Roberts

(74) *Attorney, Agent, or Firm* — Carr & Ferrell LLP; James M. Nachtwey

(57) ABSTRACT

The present technology in various embodiments discloses a composition may include an accelerant and a relaxant, the relaxant counteracting the accelerant resulting in the balanced dental care composition having an accelerant activity for a user caused by the accelerant balanced with a relaxant activity for the user caused by the relaxant. According to some embodiments, the present technology discloses a dental care composition such as a toothpaste formulation that provides iodine and cannabidiol for the combined benefits of iodine supplementation with holistic balanced energy, and the combined oral health benefits such as anti-bacterial, anti-inflammatory, teeth cleaning, and gum cleaning. Furthermore, the present technology prevents iodine deficiency for a user by providing a minimum base level of daily iodine consumption. Additionally, the present technology provides a dental composition such as a toothpaste that counteracts the high energy effects of iodine with a relaxant such as cannabidiol.

19 Claims, 4 Drawing Sheets

100

| Ingredient | Function | Weight Percentage (Preferred) | Weight Percentage (Most Preferred) |
|---|---|---|---|
| Cannabidiol (CBD) | Active Agent | 0.10-5% | 0.10-1% |
| Iodine | Active Agent | 0.001-5% | 0.001-1% |
| Water | Solvent | 20-60% | 30-40% |
| Glycerin | Humectant | 0.5-30% | 0.5-8% |
| Hydrated Silica | Soft-Abrasive | 5-30% | 8-20% |
| Sodium Lauryl Sulfate | Surfactant | 0.5-5% | 0.5-4% |
| Xylitol | Sweetening Agent | 0.5-8% | 1-5% |
| Calcium Silicate | Remineralizing Agent | 0.5-10% | 0.5-4% |
| Sodium Phosphate | Remineralizing Agent | 0.25-5% | 0.25-3% |
| Cocamidoproply Betaine | Surfactant | 0.5-3% | 0.5-2% |
| Xanthan Gum | Binder | 0.5-5% | 0.5-2% |
| Bee Propolis Extract | Active Agent | 0.1-3% | 0.5-1% |
| Sodium Saccharin | Sweetening Agent | 0.01-1% | 0.05-0.3% |
| Herbal Extracts / Natural Flavor | Flavoring Agent | 0.01-1% | 0.1-0.3% |
| Potassium Sorbate | Preservative | 0.1-1% | 0.1-0.3% |
| Hydroxyapatite | Cleaning Agent/ Remineralizing Agent | 0.5-4% | 1-2% |
| Titanium Dioxide | Coloring Agent | 0.1-2% | 0.25-2% |
| Sorbitol | Humectant/ Sweetening Agent | 40-60% | |
| Sodium Benzoate | Preservative | 0.1-0.8% | 0.3 – 0.3% |
| Carboxy-Methyl-Cellulose or Ethyl Cellulose or combinations thereof | Binder | | 0.1 – 2.% |

FIG. 1

200

| **Ingredients** | V1 (%m/m) | V2 (%m/m) |
|---|---|---|
| **Layer A** | | |
| Water | 22 - 25 | 20 -23 |
| Humectants | 52 | 63 |
| Xylitol | 4.3 | 0 |
| Xanthan Gum Pre-hydrated 0.8% | 0.2 | 0.25 |
| Hydroxy-ethyl-cellulose | 0.4 | 0.45 |
| **Layer B** | | |
| Nano Hydroxyapatite | 2 | 1.75 |
| Hydrated Silica | 10.5 | 7 |
| Coloring Agent | 0.086 | 0.084 |
| Surfactants | 1 | 0.75 |
| CBD (31 mg/g ) emulsion | 4.6 | 4 |
| Iodine (2% Sol.) in alcohol | 0.053 | 0.05 |
| Preservatives | 0.2 – 0.06 | 0.2 – 0.06 |
| Natural Flavor | 0.25 -0.6 | 0.25 -0.6 |
| TOTAL | 100 | 100 |

FIG. 2

300

| Ingredients | V3 (%m/m) |
| --- | --- |
| **Layer A** | |
| Water | 16 - 19 |
| Humectants | 65 |
| Sweetening Agent | 0.1 – 0.5 |
| Binders | 0.2 |
| Carboxymethyl Cellulose (CMC) | 0.5 |
| **Layer B** | |
| Nano Hydroxyapatite | 1 |
| Hydrated Silica | 9.4 |
| Coloring Agent | 0.06 |
| Surfactants | 0.96 |
| CBD (31 mg/g ) emulsion | 3.6 |
| Iodine (2% Sol.) in glycerin and distilled water | 0.05 |
| Preservatives | 0.2 – 0.06 |
| Natural Flavor | 0.25 -0.45 |
| TOTAL | 100 |

FIG. 3

BALANCED DENTAL CARE COMPOSITIONS AND METHODS

CROSS REFERENCE TO RELATED APPLICATIONS

This application claims the priority benefit of U.S. Provisional Patent Application Ser. No. 63/547,837 filed on Nov. 8, 2023. The aforementioned disclosure is hereby incorporated by reference in its entirety including all references cited therein.

FIELD OF TECHNOLOGY

Embodiments of the present disclosure are directed to a balanced dental care composition and methods thereof. Various embodiments include a balanced dental care toothpaste including an accelerant, and a relaxant, the relaxant counteracting the accelerant resulting in the balanced dental care composition.

BACKGROUND

Iodine, a trace element, is an essential component of thyroid hormones thyroxine (T4) and triiodothyronine (T3); all of which are critical for liver, kidney, muscle, and central nervous system function. Iodine regulates overall metabolism and plays a critical role in fetal and child neurodevelopment, as well as organ and tissue function. For the developing fetus, iodine deficiency is one of the greatest causes of intellectual disability, therefore making the adequate iodine intake of pregnant women and women of reproductive age critical. Thyroid enlargement and development of goiter as a result of long-term iodine deficiency can develop in infants, children, and adults when adaptation to chronic iodine deficiency occurs. In adults, severe iodine deficiency presents as hypothyroidism, goiter, mental disability, and decreased fertility. In children, iodine deficiency may be responsible for goiter, intellectual and physical developmental impairment, deafness, and cretinism. Regarding oral health, iodine deficiency is directly linked to dental problems due to endocrine dysfunction. This can lead to dry mouth and the potential for subsequent cavities and gum disease. In addition, inadequate amounts of iodine can lead to mouth breathing, a large and swollen tongue, as well as bite complications such as small jaws and anterior bite; thereby increasing the chances of developing sleep apnea.

To maintain homeostasis and hormone synthesis, the thyroid absorbs 50-60 μg/day (50-60 mcg/day) of iodine when supply is sufficient. The daily recommended dietary allowance (RDA) established by the Institute of Medicine (IOM) is 90 μg (90 mcg) for children 1-8 years old, 120 μg (120 mcg) for children 9-13 years old, 150 μg (150 mcg) for males and most females ages 14 and older, 220 μg (220 mcg) for pregnant women and 290 μg (290 mcg) for lactating women. The daily Tolerable Upper Intake Level (UL) for individuals over age 18 not receiving iodine for medical reasons is 1100 μg (1100 mcg). In the United States the IOM has set the UL for iodine intake at 1100 μg/day (1100 mcg/day) for adult men and women, which includes pregnant and lactating women 19 years and older, even though the consequences of excess intake are far less detrimental than not enough intake.

TABLE A

| Life Stage | Recommended Amount |
|---|---|
| Birth to 6 months | 110 mcg |
| Infants 7-12 months | 130 mcg |
| Children 1-8 years | 90 mcg |
| Children 9-13 years | 120 mcg |
| Teens 14-18 years | 150 mcg |
| Adults | 150 mcg |
| Pregnant teens and women | 220 mcg |
| Breastfeeding teens and women | 290 mcg |

Table A above provides the recommended amount of iodine based on age (in micrograms (mcg).

The human body needs iodine to function properly, but it cannot make iodine on its own. Instead, the human body needs to consume it. Iodine is mainly present in foods such as fish, seaweed, eggs, dairy, and even in the form of iodized salt (sodium iodide). For example, 100 g of hard-boiled eggs contains roughly 50 μg (50 mcg) of iodine, which would only amount to 25 μg (25 mcg) for the average weight of a single 50 g hard-boiled egg.

Sodium iodide with table salt was established in the 1920's as a way to reduce iodine deficiency. However, data from recent decades has indicated falling iodine status in the United States and an increase in iodine deficiency as having re-emerged as a global concern among populations in developed countries. With the changes in diet, topsoil erosion, less sodium iodide table salt consumption, and other factors, a new approach to prevent iodine deficiency in the United States and globally is needed.

The issue with iodine as a supplement in toothpaste is the burst of energy it provides; iodine is an accelerant. An accelerant is fine in the morning. However, iodine is not conducive to sleep at night when you want to be in a non-excited, relaxed state of mind. Niche toothpastes with accelerant active ingredients developed a toothpaste for the day, and a toothpaste for night without accelerants. However, having two separate toothpastes is too cumbersome and inconvenient, especially when traveling. It is much better and simpler to just have one toothpaste that includes a relaxant active ingredient.

Previous approaches to dental care compositions have typically focused on incorporating various active ingredients such as fluoride, hydrogen peroxide, and baking soda to promote oral health and hygiene. These compositions often aim to provide specific benefits such as whitening, cavity prevention, and plaque removal. While these compositions may be effective in targeting individual oral care needs, they may lack a balanced approach that addresses both the benefits and potential side effects of the active ingredients.

In light of the limitations of existing dental care compositions, there remains a need for a balanced dental care composition that effectively combines an accelerant and a relaxant to provide users with a harmonious oral care experience. By counteracting the effects of the accelerant with a relaxant, the balanced dental care composition described herein aims to offer users a comprehensive solution that optimizes both the nutritional health side effects of supplementation through gum and oral cavity absorption and benefits of oral care products. However, none of these approaches have provided a comprehensive solution that combines the features described in this disclosure.

SUMMARY

In some embodiments the present technology is directed to a balanced dental care composition including an accelerant; and a relaxant, the relaxant counteracting the accelerant resulting in the balanced dental care composition. In some embodiments the present technology is directed to toothpastes, and more particularly, to a toothpaste formulation that includes an accelerant (e.g., iodine) and a relaxant, (e.g., cannabidiol, also known as CBD), the relaxant counteracting the accelerant resulting in the balanced dental care composition. The toothpaste formulation can further include additional active agents and non-active agents (excipients) such as carriers, binders, thickening agents, gelling agents, emulsifiers, surfactants, flavoring agents, sweetening agents, coloring agents, preservatives, stabilizers, solvents, foaming agents, antioxidants, and other suitable excipients.

In some embodiments the present technology may include cannabidiol as an active ingredient. Cannabidiol is one of the main active molecules from the cannabis plant. CBD can be pure cannabidiol, such as synthetic cannabidiol, or a purified version of cannabidiol, which will contain other molecules from the cannabis plant, depending on the level of purification. Pure cannabidiol does not contain the psychoactive tetrahydrocannabinol (delta-9-tetrahydrocannabinol, also known as THC), which is also derived from cannabis. The cannabidiol employed in the present technology can be full spectrum (including many of the cannabinoids and compounds of the cannabis plant, including up to 0.3% THC) or broad spectrum (which includes all of the compounds of full-spectrum CBD with no detectable THC). For purposes of this application, the term cannabidiol will include full spectrum, broad spectrum, and pure cannabidiol unless otherwise indicated. There are no known abuse or dependency issues from pure cannabidiol. Cannabidiol (pure, broad spectrum and full spectrum) has been safely employed in oral and topical formulations. Cannabidiol has been shown to provide positive effects, including, but not limited to, anti-bacterial and anti-inflammatory effects in oral and topical formulations, as well as being a relaxant.

In some embodiments the present technology includes a second active agent that is iodine. In some embodiments, the iodine is nascent iodine. Nascent iodine is an organic supplement for optimal thyroid function, hormone balance, and metabolism. Furthermore, nascent iodine refers to iodine in an atomic, uncharged, highly reactive form (I). In this state, iodine (I) is not typically a negatively charged ion ($I^-$), but rather an atomic form (I), which is neutral and unbound. Nascent iodine is considered highly reactive because it is not in its more stable ionic ($I^-$) or molecular ($I_2$) state. Once nascent iodine enters the body, nascent iodine quickly reacts to form iodide ($I^-$) or combines with other molecules. Iodide ($I^-$) is the negatively charged ion, which is the form most iodine is in when it is absorbed and utilized by the body, especially in thyroid function. So, nascent iodine itself is not in the I-form, but once inside the body, nascent iodine is rapidly converted to iodide ($I^-$) or combine with other compounds to perform biological functions. Nascent Iodine, when in an atomic form, is (I) and once absorbed into the body, it will be converted to (I−).

Iodine has been shown to assist oral health including, but not limited to tooth and gum health. In addition, iodine deficiency is directly linked to causing dental problems due to endocrine dysfunction. This can lead to dry mouth, which is known to increase the risk for cavities and gum disease. The second active agent may be potassium iodide (KI), the potassium iodide (KI) being a salt with a one-to-one ratio of potassium cations (K+) and iodide anions (I−) in a crystal lattice form in some embodiments. The second active agent may also be sodium iodide (NaI), the sodium iodide (NaI) being a salt with a one-to-one ratio of sodium cations (Na+) and iodide anions ($I^-$) in a crystal lattice form, and combinations thereof.

According to some embodiments, the present technology is directed to a balanced dental care composition including an accelerant (nascent iodine); and a relaxant (cannabidiol), the relaxant (cannabidiol) counteracting the accelerant (nascent iodine) resulting in the balanced dental care composition.

Some embodiments include a balanced dental care composition, including: an accelerant; and a relaxant, the relaxant counteracting the accelerant resulting in the balanced dental care composition having an accelerant activity for a user caused by the accelerant balanced with a relaxant activity for the user caused by the relaxant.

Some embodiments include a balanced dental care composition, wherein the accelerant is iodine, the iodine being a source of iodine consumption for a user that prevents iodine deficiency for the user by providing a daily iodine consumption for the user.

Some embodiments include a balanced dental care composition, wherein iodine is nascent iodine, the nascent iodine being in an atomic, uncharged, highly reactive form (I) that is neutral and unbound.

Some embodiments include a balanced dental care composition, wherein iodine is potassium iodide (KI), the potassium iodide (KI) being a salt with a one-to-one ratio of potassium (K+) and (I−) in a form.

Some embodiments include a balanced dental care composition, wherein iodine is sodium iodide (NaI), the sodium iodide (NaI) being a salt with a one-to-one ratio of sodium (Na+) and (I−) in a form.

Some embodiments include a balanced dental care composition, wherein the iodine is 0.001 percent to 1 percent by weight relative to a total weight of the balanced dental care composition.

Some embodiments include a balanced dental care composition, wherein the iodine is 0.16 percent by weight relative to a total weight of the balanced dental care composition.

Some embodiments include a balanced dental care composition, wherein the relaxant is cannabidiol (CBD).

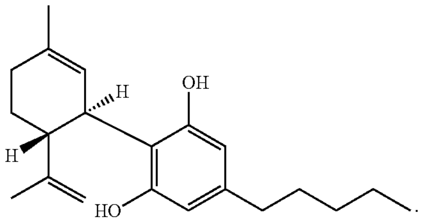

Cannabidiol (CBD)

Some embodiments include a balanced dental care composition, wherein the cannabidiol is full-spectrum cannabidiol, the full-spectrum cannabidiol including naturally occurring cannabis plant extracts including and less than 0.3 percent tetrahydrocannabinol by weight relative to a total weight of the balanced dental care composition.

Some embodiments include a balanced dental care composition, wherein the cannabidiol is broad-spectrum cannabidiol, the broad-spectrum cannabidiol including no tetrahydrocannabinol.

Some embodiments include a balanced dental care composition, wherein the cannabidiol is a cannabidiol isolate.

Some embodiments include a balanced dental care composition, wherein the cannabidiol is non-psychoactive.

Some embodiments include a balanced dental care composition, wherein the cannabidiol is 0.10 percent to 1 percent by weight relative to a total weight of the balanced dental care composition.

Some embodiments include a balanced dental care composition, wherein the balanced dental care composition is a toothpaste.

Some embodiments include a balanced dental care composition, further including at least one herbal supplement.

Some embodiments include a balanced dental care composition, wherein the at least one herbal supplement includes at least one of peppermint, spearmint, wintergreen, corn mint, rosemary, nettle, thyme, eucalyptus, slippery elm, hyssop, sage, bay laurel, juniper, lemon balm, olive, marsh mellow root, cucumber seed extract, aloe vera, chamomile, and combinations thereof.

Some embodiments include a balanced dental care composition, further including at least one of calcium silicate, sodium phosphate, hydroxyapatite, nano hydroxyapatite, and combinations thereof.

Some embodiments include a balanced dental care composition, wherein the at least one of calcium silicate, sodium phosphate, hydroxyapatite, nano hydroxyapatite, and combinations thereof is between 1 to 3 percent by weight relative to a total weight of the balanced dental care composition.

Some embodiments include a balanced dental care composition, wherein the accelerant is iodine, the iodine being 0.001 percent to 1 percent by weight relative to a total weight of the balanced dental care composition, the iodine being nascent iodine, the nascent iodine being in an atomic, uncharged, highly reactive form (I) that is neutral and unbound; and wherein the relaxant is cannabidiol, the cannabidiol being 0.10 percent to 1 percent by weight relative to the total weight of the balanced dental care composition.

Some embodiments include a balanced dental care composition, including: iodine: 0.001-1 percent by weight relative to a total weight of the balanced dental care composition; cannabidiol 0.10-1 percent by weight relative to the total weight of the balanced dental care composition; water: 20-60 percent by weight relative to the total weight of the balanced dental care composition; sorbitol: 40-60 percent by weight relative to the total weight of the balanced dental care composition; glycerin: 0.5-8 percent by weight relative to the total weight of the balanced dental care composition; hydrated silica: 8-20 percent by weight relative to the total weight of the balanced dental care composition; sodium lauryl sulfate: 0.5-5 percent by weight relative to the total weight of the balanced dental care composition; xylitol: 1-5 percent by weight relative to the total weight of the balanced dental care composition; calcium silicate: 0.5-4 percent by weight relative to the total weight of the balanced dental care composition; sodium phosphate: 0.25-3 percent by weight relative to the total weight of the balanced dental care composition; cocamidopropyl betaine: 0.5-2% or 0.5-3 percent by weight relative to the total weight of the balanced dental care composition; xanthan gum: 0.05-2 percent by weight relative to the total weight of the balanced dental care composition; titanium dioxide: 0.1-2% or 0.25-2 percent by weight relative to the total weight of the balanced dental care composition; hydroxyapatite: 1-2%, or nano hydroyapatite percent by weight relative to the total weight of the balanced dental care composition; carboxy-methyl-cellulose: 0.1-2 percent by weight relative to the total weight of the balanced dental care composition; bee propolis extract: 0.5-1 percent by weight relative to the total weight of the balanced dental care composition; sodium saccharin: 0.05-0.3 percent by weight relative to the total weight of the balanced dental care composition; natural flavor: 0.1-1.5 percent by weight relative to the total weight of the balanced dental care composition; potassium sorbate: 0.1-0.3 percent by weight relative to the total weight of the balanced dental care composition; and sodium benzoate: 0.1-0.3 percent by weight relative to the total weight of the balanced dental care composition.

Some embodiments include a balanced dental care composition, including: iodine: 0.001-1 percent by weight relative to a total weight of the balanced dental care composition; cannabidiol: 0.10-1 percent by weight relative to the total weight of the balanced dental care composition; solvent: 20-60 percent by weight relative to the total weight of the balanced dental care composition; a first humectant: 40-60 percent by weight relative to the total weight of the balanced dental care composition; a second humectant: 0.5-8 percent by weight relative to the total weight of the balanced dental care composition; an abrasive: 8-20 percent by weight relative to the total weight of the balanced dental care composition; a first surfactant: 0.5-5 percent by weight relative to the total weight of the balanced dental care composition; a second surfactant: 0.5-2 percent or 0.5-3 percent by weight relative to the total weight of the balanced dental care composition; a first sweetening agent: 1-5 percent by weight relative to the total weight of the balanced dental care composition; a second sweetening agent: 0.05-0.3 percent by weight relative to the total weight of the balanced dental care composition; a first remineralizing agent: 0.5-4 percent by weight relative to the total weight of the balanced dental care composition; a second remineralizing agent: 0.25-3 percent by weight relative to the total weight of the balanced dental care composition; a first binder: 0.05-2 percent by weight relative to the total weight of the balanced dental care composition; a second binder: 0.1-2 percent by weight relative to the total weight of the balanced dental care composition; a coloring agent: 0.1-2 percent or 0.25-2 percent by weight relative to the total weight of the balanced dental care composition; a cleaning agent: 1-3 percent by weight relative to the total weight of the balanced dental care composition; an active agent: 0.5-1 percent by weight relative to the total weight of the balanced dental care composition; natural flavor: 0.1-1.5 percent by weight relative to the total weight of the balanced dental care composition; a first preservative: 0.1-0.3 percent by weight relative to the total weight of the balanced dental care composition; and a second preservative: 0.1-0.3 percent by weight relative to the total weight of the balanced dental care composition.

These and other objects, features, and advantages of the present technology will become more readily apparent from the attached drawings and the detailed description of the preferred embodiments, which follow.

BRIEF DESCRIPTION OF THE DRAWINGS

The accompanying drawings, where like reference numerals refer to identical or functionally similar elements throughout the separate views, together with the detailed description below, are incorporated in and form part of the specification, and serve to further illustrate embodiments of concepts that include the claimed disclosure, and explain various principles and advantages of those embodiments.

FIG. 1 illustrates Table 1 that shows compositions of a toothpaste including an accelerant (iodine); and a relaxant (cannabidiol), the relaxant counteracting the accelerant resulting in the balanced dental care composition and Table 1 further shows a "CBD Iodine Formula" with specific percentages of ingredients, according to the subject disclosure.

FIG. 2 illustrates Table 2 that shows compositions of a toothpaste including an accelerant (iodine); and a relaxant (cannabidiol), the relaxant counteracting the accelerant resulting in the balanced dental care composition, according to the subject disclosure.

FIG. 3 illustrates Table 3 that shows compositions of a toothpaste including an accelerant (iodine); and a relaxant (cannabidiol), the relaxant counteracting the accelerant resulting in the balanced dental care composition, according to the subject disclosure.

DESCRIPTION OF EXEMPLARY EMBODIMENTS

Figure 4:
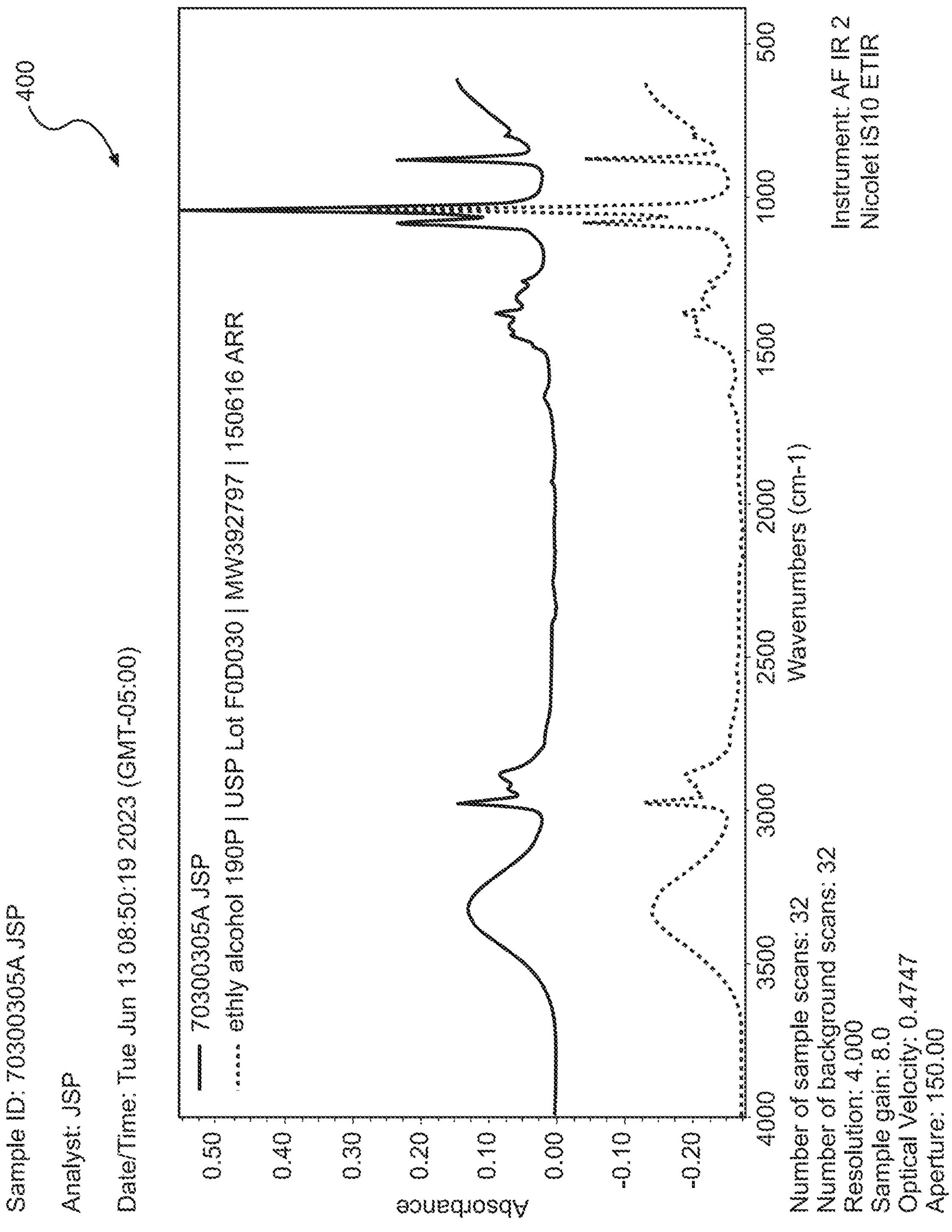
FIG. 4 shows the spectra of nascent iodine with ethyl alcohol and the nascent iodine that is used in toothpaste compositions of the present technology as an accelerant, according to the subject disclosure.

Embodiments of the present disclosure, in general terms, are directed to a dental care composition that includes an accelerant and a relaxant. The relaxant counteracts the effects of the accelerant, resulting in a balanced dental care product that maintains the health of a user by balancing the activities caused by the accelerant and relaxant. Advantageously, the present technology addresses the problem of iodine deficiency, oral health issues such as bacterial infections and inflammation, and the removal of plaque and tartar, while also providing balanced energy and catering to individuals with oral sensitivities through a unique toothpaste formulation enriched with iodine and cannabidiol.

The field of dental care has seen significant advancements over the years, with a focus on improving oral health and hygiene. Dental care compositions, such as toothpaste, have been a cornerstone of these advancements, providing a means to clean and protect teeth and gums from various oral diseases. These compositions typically include a variety of ingredients designed to enhance oral health, including abrasives to remove plaque and tartar, fluoride to prevent tooth decay, and flavoring agents to improve taste and encourage regular use. In recent years, there has been a growing interest in the development of dental care compositions that not only clean and protect the teeth and gums, but also provide additional health benefits. These compositions aim to leverage the regular use of dental care products as a delivery mechanism for these additional health benefits. However, the inclusion of these active ingredients in dental care compositions is not without challenges. For example, the inclusion of these ingredients must be balanced with the need for the composition to effectively clean the teeth and gums, and to be safe for regular use and to have balanced effects on users. Furthermore, there is a need for dental care compositions that include anticaries agents other than fluoride, particularly for individuals with oral sensitivities. While fluoride is a common ingredient in many dental care compositions due to its proven effectiveness in preventing tooth decay, some individuals are sensitive to fluoride and may experience adverse reactions. In light of these considerations, there is a clear need for improvements in dental care compositions. These improvements should aim to overcome the shortcomings of existing implementations, providing a balanced dental care composition that effectively cleans and protects the teeth and gums, while also delivering additional balanced health benefits such as iodine supplementation through gum and oral cavity absorption.

In various embodiments, the present technology discloses a toothpaste formulation that provides iodine and cannabidiol for the combined benefits of iodine supplementation with holistic balanced energy, and the combined oral health benefits such as anti-bacterial, anti-inflammatory, teeth cleaning, and gum cleaning. Furthermore, the present technology prevents iodine deficiency by providing a base level of daily iodine consumption. Additionally, the present technology provides a dental composition such as a toothpaste that counteracts the high energy effects of iodine with a relaxant such as cannabidiol. Moreover, the present technology provides a toothpaste formulation that is effective at removing plaque and tartar from the teeth and gums with the other benefits associated with cannabidiol. Furthermore, the present technology discloses a toothpaste formulation that includes anticaries agents (other than fluoride) to people with oral sensitivities.

Advantageously, the balanced dental care composition provides a unique combination of an accelerant and a relaxant. This combination is designed to provide the user with a balanced energy state. The accelerant, in this case iodine, provides a boost of energy to the user. Iodine is also known for its antibacterial properties, which contribute to oral health by combating harmful bacteria in the mouth. On the other hand, the relaxant, such as cannabidiol, counteracts the high energy effects of the iodine, providing a calming effect. This balance of energy is particularly beneficial for users who may be sensitive to high energy effects of iodine. Furthermore, cannabidiol is known for its anti-inflammatory properties, which can help to reduce inflammation in the gums and other areas of the mouth.

Advantageously, the use of iodine as an accelerant in the dental care composition not only provides energy to the user but also contributes to the prevention of iodine deficiency. Iodine deficiency is a common issue that can lead to various health problems. By incorporating iodine into the dental care composition, the present technology helps a user with a minimum base level of daily iodine consumption, thereby helping to prevent iodine deficiency for users. Additionally, iodine is known for its antibacterial properties, which can help to maintain oral health by combating harmful bacteria in the mouth.

Advantageously, the inclusion of iodine in the dental care composition in an amount of 0.001 to 1 percent by weight helps a user receive an amount of iodine for daily consumption while also benefiting from the antibacterial properties of iodine. This concentration of iodine is effective in providing the desired energy boost and antibacterial effects without causing any adverse effects to the user. The balanced dental care composition thus provides a safe and effective means of iodine supplementation and oral health maintenance.

Not only is iodine necessary for healthy bodily function of optimal thyroid function, hormone balance, and metabolism, iodine also is extremely beneficial at preventing tooth decay and gum disease.

Typical modern toothpaste formulations on the market do not contain active ingredients that provide iodine supplementation. Typical modern toothpaste formulations contain active ingredients that provide fluoride and sometimes teeth whitening materials. The non-active ingredients generally include a mixture of solvents, flavoring agents, sweeteners, coloring agents, fillers, surfactants, and other excipients to aid the formulation.

Conventional toothpastes contain fluoride with or without additional teeth whitening agents. The remainder of the toothpaste formulation is generally directed to providing a non-abrasive gel formulation that has good shelf life, good flowability, and a pleasing taste for the consumer. Unfortunately, the limited active agents available for commercial toothpastes fail to satisfy iodine supplementation, and many other oral health needs.

The issue with iodine as a supplement in toothpaste is the burst of energy it provides; iodine is an accelerant. An accelerant is fine in the morning. However, iodine is not conducive to sleep at night when you want to be in a non-excited, relaxed state of mind. Niche toothpastes with accelerant active ingredients developed a toothpaste for the day, and a toothpaste for night without accelerants. But this method of having two separate toothpastes is too cumbersome, and inconvenient especially when traveling. It is much better and simpler to just have one toothpaste. In order to avoid two separate toothpastes with one toothpaste for the day and one toothpaste for the night, a relaxant active ingredient will have to be used. Cannabidiol is commonly used as an effective sleep aid.

Cannabidiol is effective at inhibiting the production of cortisol in the adrenal gland associated with an excited state of mind, or a stress response. In recent years, cannabidiol was introduced in the first pharmaceutical drug to treat epilepsy because it was so effective at inhibiting cortisol production, preventing seizures.

In order to offset the accelerant properties of iodine, cannabidiol is incorporated as a relaxant to counteract iodine in various embodiments of the present technology. This creates a holistic balance; figuratively, iodine is the “yin” and cannabidiol is the “yang”. Both iodine and cannabidiol affect the overall health and energy levels of the user even at small dosage levels. Together, iodine and cannabidiol create a balance without the high energy spike or low energy crash. A person can brush their teeth at any time of day and receive a balanced, neutral energy level from their toothpaste, while absorbing all the mineral, herbal, and oral health benefits included in the toothpaste formula with the active ingredients of iodine and cannabidiol. Cannabidiol can be employed as an active agent in the toothpaste formulations of the present invention. The use of cannabidiol provides benefits to the toothpaste formulations that go beyond that of oral health. Specifically, cannabidiol has been shown to provide assistance with anxiety, insomnia, chronic pain, inflammation and dependency. The cannabidiol and can be present from 17 mg to 1500 mg, preferably from 100 to 500 mg, and most preferably about 250 mg. Embodiments of the toothpaste formulation can include 0.1-5 percent by weight of the toothpaste formulation of cannabidiol, and more preferably 0.10-1 by weight relative to a total weight of the balanced dental care composition.

In some embodiments, additional active agents that can be employed in the toothpaste formation include, but are not limited to, bee propolis extract, sodium phosphate, calcium silicate, iodine, hydroxyapatite, nano hydroxyapatite, and combinations thereof. Some embodiments of the balanced dental care composition comprise 0.5-4 percent of calcium silicate by weight relative to a total weight of the balanced dental care composition. Some embodiments of the balanced dental care composition comprise 1-2 percent of Hydroxyapatite or Nano Hydroxyapatite by weight relative to a total weight of the balanced dental care composition. Some embodiments of the balanced dental care composition comprise 0.25-3 percent of Sodium Phosphate by weight relative to a total weight of the balanced dental care composition. Some embodiments of the balanced dental care composition comprise Bee Propolis Extract: 0.5-1 percent by weight relative to a total weight of the balanced dental care composition.

In some embodiments, compositions of the present technology include Bee propolis extract that has anti-tumor and anti-cancer properties, which have been shown to assist with cleaning teeth by killing bacteria in the oral cavity. Bee propolis extract provides the added benefit of being a natural extract devoid of harsh chemical additives often found in commercial toothpastes.

Various embodiments of the present technology include phosphate and calcium silicate that can be viewed as excipients that provide stability and other benefits to the toothpaste formulations, both compounds also provide a remineralizing effect for enamel protection.

Some embodiments of the present technology include Iodine to provide protection from tooth decay and that acts as an accelerant. Various forms of iodine can be used as anticaries agents in a similar manner to fluoride in commercial toothpaste formulations. This reduces the overall exposure to fluoride associated with toothpastes, mouthwashes, and public water. The preferred iodine is nascent iodine. Alternative iodine compounds can be employed including, but not limited to, nascent iodine, sodium and potassium salts, inorganic iodine, iodate, iodide, and combinations thereof. Some embodiments of the balanced dental care composition comprise 0.15-1 percent of Iodine by weight relative to a total weight of the balanced dental care composition.

In some embodiments the present technology includes nascent iodine. Nascent iodine is an organic supplement for optimal thyroid function, hormone balance, and metabolism. Furthermore, nascent iodine refers to iodine in an atomic, uncharged, highly reactive form (I). In this state, iodine (I) is not typically a negatively charged ion ($I^-$), but rather an atomic form (I), which is neutral and unbound. Nascent iodine is considered highly reactive because it is not in its more stable ionic ($I^-$) or molecular ($I_2$) state. Once nascent iodine enters the body, nascent iodine quickly reacts to form iodide ($I^-$) or combines with other molecules. Iodide ($I^-$) is the negatively charged ion, which is the form most iodine is in when it is absorbed and utilized by the body, especially in thyroid function. So, nascent iodine itself is not in the $I^-$ form, but once inside the body, nascent iodine is rapidly converted to iodide ($I^-$) or combine with other compounds to perform biological functions. Nascent Iodine, when in an atomic form, is (I) and once absorbed into the body, it will be converted to ($I^-$). There are two forms of nascent iodine, the form of iodine (I) mixed with ethyl alcohol, and other form of iodine (I) mixed with glycerin and distilled water.

Various embodiments of the present technology include a humectant. Humectants are stabilizers that retain moisture in the toothpaste formulation, resist drying out of the toothpaste formulation in the tube or other packaging and improve flowability of the toothpaste formulation. Additionally, humectants prevent dryness in the oral cavity during brushing. Further, humectants such as glycerin and sorbitol have been shown to inhibit bacterial growth in the oral cavity. Preferred humectants are glycerin and sorbitol. Additional humectant that can be included in the present formulation include, but are not limited to, propylene glycol, pentanol and glycerol. Some embodiments of the balanced dental care composition comprise 0.5-8 percent of glycerin by weight relative to a total weight of the balanced dental care composition and sorbitol and 40-60 percent by weight relative to a total weight of the balanced dental care composition.

Various embodiments of the present technology include abrasive agents, preferably soft-abrasive agents, can be included in the toothpaste formulation to provide cleaning, scouring, and removal of stains from enamel, as well as removal of plaque and tartar without the use of harsh abrasives. A preferred abrasive agent is hydrated silica. Other suitable abrasive agents include, but are not limited to, hydroxyapatite, nano hydroxyapatite, sodium bicarbonate, aluminum oxide, calcium carbonate, magnesium carbonate, calcium pyrophosphate and combinations thereof. Some embodiments of the balanced dental care composition comprise 8-20 percent of hydrated silica by weight relative to a total weight of the balanced dental care composition.

Some embodiments of the present technology include surfactants employed in the toothpaste formulation to provide stability to the toothpaste formulation and to aid in the foaming of the toothpaste when used to clean teeth and gums. The preferred surfactants for use in the toothpaste formulation are sodium lauryl sulfate and cocamidopropyl betaine. Other suitable surfactants include, but are not limited to, sodium lauryl sulfoacetate, sodium lauroyl sarcosinate, sodium cocoyl glutamate, disodium cocoyl glutamate, sodium methyl cocoyl taurate, sodium lauryl sarcosinate, sodium alkylsulfo succinate, sodium cocomonoglyceride sulfonate, lauryl glucoside, sodium cocoamphoacetate, sodium lauryl glucose carboxylate and sucrose fatty acid esters. Some embodiments of the balanced dental care composition comprise the following percentages by weight relative to a total weight of the balanced dental care composition as follows Sodium Lauryl Sulfate: 0.5-5%, or Sodium Lauroyl Sarcosinate: 0.5-5% or Sodium Lauryl Sulfoacetate (SLSA): 0.5-5% (Alternative 1), or Sodium Cocoyl Glutamate: 0.5-4% (Alternative 2), or Disodium Cocoyl Glutamate: 0.5-4% (Alternative 3), or combinations thereof.

Some embodiments of the present technology include sweetening agents that can be employed in the toothpaste formulation to provide greater patient compliance and improved taste without the negative effects associated with sugar. The preferred sweetening agents include xylitol and sodium saccharin. Other suitable sweetening agents include, but are not limited to, sucralose, sorbitol, glycerol, and other non-sugar sweeteners. Some embodiments of the balanced dental care composition comprise 40-60 percent of Sorbitol by weight relative to a total weight of the balanced dental care composition. Some embodiments of the balanced dental care composition comprise 1-5 percent of Xylitol by weight relative to a total weight of the balanced dental care composition. Some embodiments of the balanced dental care composition comprise Sodium Saccharin 0.05-0.3 percent by weight relative to a total weight of the balanced dental care composition.

Some embodiments of the present technology include flavoring agents that can be employed in the toothpaste formulation to provide additional taste, breath-freshening and/or other effervescent qualities. Flavoring agents can improve taste, mouthfeel, breath, and patient compliance. Flavoring agents can include, but are not limited to herbal extracts, such as peppermint, spearmint, wintergreen, corn mint, rosemary, nettle, thyme, eucalyptus, slippery elm, hyssop, sage, bay laurel, juniper, lemon balm, olive, marsh mellow root, cucumber seed extract, aloe vera, chamomile, mint, and combinations thereof.

Various embodiments of the present technology include binders that can be employed in the toothpaste formulation to thicken the toothpaste formulation forming a paste consistency. The binders further assist in retaining the additional excipients and active agents in the toothpaste formulation. A preferred binder is xanthan gum. Other suitable binders include, but are not limited to, mineral colloids, other natural gums, carrageenan, synthetic cellulose, and combinations thereof. Some embodiments of the balanced dental care composition comprise 0.05-2 percent of Xanthan Gum by weight relative to a total weight of the balanced dental care composition. Some embodiments of the balanced dental care composition comprise carboxy-Methyl-Cellulose 0.1-2 percent or Ethyl Cellulose 0.1-2 percent by weight relative to a total weight of the balanced dental care composition or combinations thereof.

Various embodiments of the present technology include preservatives that can be employed in the toothpaste formulation to add stability and improve shelf life. A preferred preservative is potassium sorbate. Other suitable preservatives include, but are not limited to, sodium benzoate, and combinations thereof.

Some embodiments of the balanced dental care composition comprise Potassium Sorbate 0.1-0.3 percent by weight relative to a total weight of the balanced dental care composition. Some embodiments of the balanced dental care composition comprise Sodium Benzoate 0.1-0.3 percent by weight relative to a total weight of the balanced dental care composition.

Some embodiments of the present technology include a primary solvent and/or carrier for the toothpaste formulation that is water. Water provides for the flowability of the toothpaste formulation, hydration of the binders and delivery of the active agents to the teeth and gums. Some embodiments of the balanced dental care composition comprise 20-60 percent by weight relative to a total weight of the balanced dental care composition.

Various embodiments of the present technology include the toothpaste formulation further including additional excipients, such as gelling agents, thickening agents, coloring agents (such as titanium dioxide), additional anticaries agents (such as hydroxyapatite), additional anti-plaque agents, additional enamel protectors, and other suitable excipients for formulating toothpaste. Some embodiments of the balanced dental care composition comprise 0.1-2 percent or 0.25-2 percent of Titanium Dioxide by weight relative to a total weight of the balanced dental care composition.

FIG. 1 illustrates Table 1 (100) that shows compositions of a toothpaste including an accelerant (iodine); and a relaxant (cannabidiol), the relaxant counteracting the accelerant resulting in the balanced dental care composition and Table 1 further shows a "CBD Iodine Formula" with specific percentages of ingredients, according to the subject disclosure as shown below in Table 1.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material.

TABLE 1

| Ingredient | Function | Weight Percentage (Preferred) | Weight Percentage (Most Preferred) |
|---|---|---|---|
| Cannabidiol (CBD) | Active Agent | 0.10-5% | 0.10-1% |

TABLE 1-continued

| Ingredient | Function | Weight Percentage (Preferred) | Weight Percentage (Most Preferred) |
|---|---|---|---|
| Iodine | Active Agent | 0.001-5% | 0.001-1% |
| Water | Solvent | 20-60% | 30-40% |
| Glycerin | Humectant | 0.5-30% | 0.5-8% |
| Hydrated Silica | Soft-Abrasive | 5-30% | 8-20% |
| Sodium Lauryl Sulfate | Surfactant | 0.5-5% | 0.5-4% |
| Xylitol | Sweetening Agent | 0.5-8% | 1-5% |
| Calcium Silicate | Remineralizing Agent | 0.5-10% | 0.5-4% |
| Sodium Phosphate | Remineralizing Agent | 0.25-5% | 0.25-3% |
| Cocamidopropyk Betaine | Surfactant | 0.5-3% | 0.5-2% |
| Xanthan Gum | Binder | 0.5-5% | 0.5-2% |
| Bee Propolis Extract | Active Agent | 0.1-3% | 0.5-1% |
| Sodium Saccharin | Sweetening Agent | 0.01-1% | 0.05-0.3% |
| Herbal Extracts/ Natural Flavor | Flavoring Agent | 0.01-1% | 0.1-0.3% |
| Potassium Sorbate | Preservative | 0.1-1% | 0.1-0.3% |
| Hydroxyapatite | Cleaning Agent/ Remineralizing Agent | 0.5-4% | 1-2% |
| Titanium Dioxide | Coloring Agent | 0.1-2% | 0.25-2% |
| Sorbitol | Humectant/ Sweetening Agent | 40-60% | |
| Sodium Benzoate | Preservative | 0.1-0.8% | 0.3-0.3% |
| Carboxy-Methyl-Cellulose or Ethyl Cellulose or combinations thereof | Binder | | 0.1-2.% |

Table 1 shows a balanced dental care composition, comprising the ingredients above comprising a "CBD Iodine Formula", according to various embodiments of the present technology.

According to various embodiments of the present technology the "CBD Iodine Formula" further comprises Sodium Lauryl Sulfate or Sodium Lauroyl Sarcosinate or Sodium Lauryl Sulfoacetate (SLSA) or Sodium Cocoyl Glutamate or Disodium Cocoyl Glutamate or Lauryl Glucoside or combinations thereof.

According to various embodiments of the present technology the "CBD Iodine Formula" further comprises calcium silicate, sodium phosphate, hydroxyapatite, and nano hydroxyapatite, or combinations thereof. For example, the "CBD Iodine Formula" may include the following exemplary combinations:

Calcium Silicate, Sodium Phosphate, and Hydroxyapatite.

Calcium Silicate, Sodium Phosphate.

Calcium Silicate.

Calcium Silicate, Hydroxyapatite.

Calcium Silicate, Sodium Phosphate, and Nano Hydroxyapatite.

EXAMPLES

The following tables depict exemplary formulations of the present technology, referring to Table 2 and Table 3 (also illustrated as FIG. 2 and FIG. 3 respectively), that are example toothpaste formulations comprising an accelerant (iodine); and a relaxant (cannabidiol), the relaxant counteracting the accelerant resulting in the balanced dental care composition having an accelerant activity for a user caused by the accelerant balanced with a relaxant activity for the user caused by the relaxant according to various embodiments of the present technology.

FIG. 2 illustrates Table 2 (200) that shows compositions of toothpaste formulations including an accelerant (iodine); and a relaxant (cannabidiol), the relaxant counteracting the accelerant resulting in the balanced dental care composition, according to the subject disclosure.

FIG. 3 illustrates Table 3 (300) that shows further compositions of toothpaste formulations including an accelerant (iodine); and a relaxant (cannabidiol), the relaxant counteracting the accelerant resulting in the balanced dental care composition, according to the subject disclosure.

| Ingredients | V1 (% m/m) | V2 (% m/m) |
|---|---|---|
| Layer A | | |
| Water | 22-25 | 20-23 |
| Humectants | 52 | 63 |
| Xylitol | 4.3 | 0 |
| Xanthan Gum Pre-hydrated 0.8% | 0.2 | 0.25 |
| Hydroxy-ethyl-cellulose | 0.4 | 0.45 |
| Layer B | | |
| Nano Hydroxyapatite | 2 | 1.75 |
| Hydrated Silica | 10.5 | 7 |
| Coloring Agent | 0.086 | 0.084 |
| Surfactants | 1 | 0.75 |
| CBD (31 mg/g) emulsion | 4.6 | 4 |
| Iodine (2% Sol.) in alcohol | 0.053 | 0.05 |
| Preservatives | 0.2-0.06 | 0.2-0.06 |
| Natural Flavor | 0.25-0.6 | 0.25-0.6 |
| TOTAL | 100 | 100 |

| Ingredients | V3 (% m/m) |
|---|---|
| Layer A | |
| Water | 16-19 |
| Humectants | 65 |
| Sweetening Agent | 0.1-0.5 |
| Binders | 0.2 |
| Carboxymethyl Cellulose (CMC) | 0.5 |
| Layer B | |
| Nano Hydroxyapatite | 1 |
| Hydrated Silica | 9.4 |
| Coloring Agent | 0.06 |
| Surfactants | 0.96 |
| CBD (31 mg/g) emulsion | 3.6 |
| Iodine (2% Sol.) in glycerin and distilled water | 0.05 |
| Preservatives | 0.2-0.06 |
| Natural Flavor | 0.25-0.45 |
| TOTAL | 100 |

In some embodiments the CBD is emulsified (250 mg per 6 oz) in the example toothpaste formulations described herein.

In some embodiments the iodine is in ethyl alcohol in the example toothpaste formulations described herein. In some embodiments the iodine is in glycerin and distilled water in the example toothpaste formulations described herein.

In some embodiments base toothpaste ingredients comprise the following in the example toothpaste formulations described herein: Water, Humectants, Xylitol, Xanthan gum prehydrated 0.8%, Hydroxyethyl cellulose, Carboxymethyl cellulose (CMC), Coloring Agent, and Preservatives.

In some embodiments, the sorbitol may be sorbitol in powder form, or liquid sorbitol 70% concentration solution.

In some embodiments cleaning toothpaste ingredients comprise the following in the example toothpaste formulations described herein: Nano Hydroxyapatite, and hydrated silica.

In some embodiments foaming toothpaste ingredients comprise the following Surfactants in the example toothpaste formulations described herein: SLS, SLSA, and Coco betaine.

In some embodiments flavoring pure natural essential oils toothpaste ingredients comprise the following in the example toothpaste formulations described herein: Peppermint EO, Spearmint EO, Melissa EO (Lemon balm), and Wintergreen EO.

In some embodiments ingredients comprise the following sweetening agent in the example toothpaste formulations described herein: sodium saccharin.

FIG. 4 shows the spectra 400 of nascent iodine with ethyl alcohol and the nascent iodine is used in toothpaste compositions of the present technology as an accelerant, according to the subject disclosure.

Some embodiments include a balanced dental care composition, comprising: an accelerant; and a relaxant, the relaxant counteracting the accelerant resulting in the balanced dental care composition having an accelerant activity for a user caused by the accelerant balanced with a relaxant activity for the user caused by the relaxant.

In some embodiments the accelerant is iodine, the iodine being a source of iodine consumption for a user that prevents iodine deficiency for the user by providing a daily iodine consumption for the user.

In some embodiments iodine is nascent iodine, the nascent iodine being in an atomic, uncharged, highly reactive form (I) that is neutral and unbound.

In some embodiments iodine is potassium iodide (KI), the potassium iodide (KI) being a salt with a one-to-one ratio of potassium (K+) and (I−) in a form.

In some embodiments the iodine is sodium iodide (NaI), the sodium iodide (NaI) being a salt with a one-to-one ratio of sodium (Na+) and (I−) in a form.

In some embodiments the iodine is 0.001 percent to 1 percent by weight relative to a total weight of the balanced dental care composition.

In some embodiments the iodine is 0.16 percent by weight relative to a total weight of the balanced dental care composition.

In some embodiments the relaxant is cannabidiol (CBD).

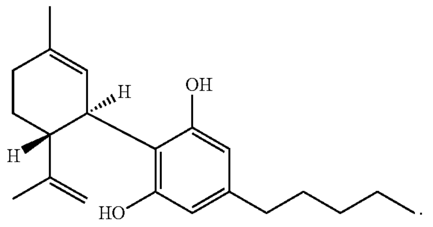

Cannabidiol (CBD)

In some embodiments the cannabidiol is full-spectrum cannabidiol, the full-spectrum cannabidiol comprising naturally occurring cannabis plant extracts including and less than 0.3 percent tetrahydrocannabinol by weight relative to a total weight of the balanced dental care composition.

In some embodiments the cannabidiol is broad-spectrum cannabidiol, the broad-spectrum cannabidiol comprising no tetrahydrocannabinol.

In some embodiments the cannabidiol is a cannabidiol isolate.

In some embodiments the cannabidiol is non-psychoactive.

In some embodiments the cannabidiol is 0.10 percent to 1 percent by weight relative to a total weight of the balanced dental care composition.

In some embodiments the balanced dental care composition is a toothpaste.

Some embodiments further comprise at least one herbal supplement.

In some embodiments the at least one herbal supplement comprises at least one of peppermint, spearmint, wintergreen, corn mint, rosemary, nettle, thyme, eucalyptus, slippery elm, hyssop, sage, bay laurel, juniper, lemon balm, olive, marshmallow root, cucumber seed extract, aloe vera, chamomile, and combinations thereof.

Some embodiments further comprise at least one of calcium silicate, sodium phosphate, hydroxyapatite, nano hydroxyapatite, and combinations thereof.

In some embodiments the at least one of calcium silicate, sodium phosphate, hydroxyapatite, nano hydroxyapatite, and combinations thereof is between 1 to 3 percent by weight relative to a total weight of the balanced dental care composition.

In some embodiments the accelerant is iodine, the iodine being 0.001 percent to 1 percent by weight relative to a total weight of the balanced dental care composition, the iodine being nascent iodine, the nascent iodine being in an atomic, uncharged, highly reactive form (I) that is neutral and unbound; and wherein the relaxant is cannabidiol, the cannabidiol being 0.10 percent to 1 percent by weight relative to the total weight of the balanced dental care composition.

Some embodiments include a balanced dental care composition, comprising: iodine: 0.001-1 percent by weight relative to a total weight of the balanced dental care composition; cannabidiol 0.10-1 percent by weight relative to the total weight of the balanced dental care composition; water: 20-60 percent by weight relative to the total weight of the balanced dental care composition; sorbitol: 40-60 percent by weight relative to the total weight of the balanced dental care composition; glycerin: 0.5-8 percent by weight relative to the total weight of the balanced dental care composition; hydrated silica: 8-20 percent by weight relative to the total weight of the balanced dental care composition; sodium lauryl sulfate: 0.5-5 percent by weight relative to the total weight of the balanced dental care composition; xylitol: 1-5 percent by weight relative to the total weight of the balanced dental care composition; calcium silicate: 0.5-4 percent by weight relative to the total weight of the balanced dental care composition; sodium phosphate: 0.25-3 percent by weight relative to the total weight of the balanced dental care composition; cocamidopropyl betaine: 0.5-2% or 0.5-3 percent by weight relative to the total weight of the balanced dental care composition; xanthan gum: 0.05-2 percent by weight relative to the total weight of the balanced dental care composition; titanium dioxide: 0.1-2% or 0.25-2 percent by weight relative to the total weight of the balanced dental care composition; hydroxyapatite: 1-2%, or nano hydroyapatite percent by weight relative to the total weight of the balanced dental care composition; carboxy-methyl-cellulose: 0.1-2 percent by weight relative to the total weight of the balanced dental care composition; bee propolis extract: 0.5-1 percent by weight relative to the total weight of the balanced dental care composition; sodium saccharin: 0.05-0.3 percent by weight relative to the total weight of the balanced dental care composition; natural flavor: 0.1-1.5 percent by weight relative to the total weight of the balanced dental care composition; potassium sorbate: 0.1-0.3 percent by weight relative to the total weight of the balanced dental care composition; and sodium benzoate: 0.1-0.3 percent by weight relative to the total weight of the balanced dental care composition.

Some embodiments include a balanced dental care composition, comprising: iodine: 0.001-1 percent by weight relative to a total weight of the balanced dental care composition; cannabidiol: 0.10-1 percent by weight relative to the total weight of the balanced dental care composition; solvent: 20-60 percent by weight relative to the total weight of the balanced dental care composition; a first humectant: 40-60 percent by weight relative to the total weight of the balanced dental care composition; a second humectant: 0.5-8 percent by weight relative to the total weight of the balanced dental care composition; an abrasive: 8-20 percent by weight relative to the total weight of the balanced dental care composition; a first surfactant: 0.5-5 percent by weight relative to the total weight of the balanced dental care composition; a second surfactant: 0.5-2 percent or 0.5-3 percent by weight relative to the total weight of the balanced dental care composition; a first sweetening agent: 1-5 percent by weight relative to the total weight of the balanced dental care composition; a second sweetening agent: 0.05-0.3 percent by weight relative to the total weight of the balanced dental care composition; a first remineralizing agent: 0.5-4 percent by weight relative to the total weight of the balanced dental care composition; a second remineralizing agent: 0.25-3 percent by weight relative to the total weight of the balanced dental care composition; a first binder: 0.05-2 percent by weight relative to the total weight of the balanced dental care composition; a second binder: 0.1-2 percent by weight relative to the total weight of the balanced dental care composition; a coloring agent: 0.1-2 percent or 0.25-2 percent by weight relative to the total weight of the balanced dental care composition; a cleaning agent: 1-3 percent by weight relative to the total weight of the balanced dental care composition; an active agent: 0.5-1 percent by weight relative to the total weight of the balanced dental care composition; natural flavor: 0.1-1.5 percent by weight relative to the total weight of the balanced dental care composition; a first preservative: 0.1-0.3 percent by weight relative to the total weight of the balanced dental care composition; and a second preservative: 0.1-0.3 percent by weight relative to the total weight of the balanced dental care composition.

As used throughout, ranges are used as shorthand for describing each and every value that is within the range. Any value within the range can be selected as the terminus of the range. In addition, all references cited herein are hereby incorporated by reference in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material.

While this technology is susceptible of embodiments in many different forms, has been described in detail several specific embodiments with the understanding that the present disclosure is to be considered as an exemplification of the principles of the technology and is not intended to limit the technology to the embodiments illustrated.

The terminology used herein is for the purpose of describing particular embodiments only and is not intended to be necessarily limiting of the disclosure. As used herein, the singular forms "a," "an" and "the" are intended to include the plural forms as well, unless the context clearly indicates otherwise. The terms "comprises," "includes" and/or "comprising," "including" when used in this specification, specify the presence of stated features, integers, steps, operations, elements, and/or components, but do not preclude the presence or addition of one or more other features, integers, steps, operations, elements, components, and/or groups thereof.

The description of the present disclosure has been presented for purposes of illustration and description, but is not intended to be exhaustive or limited to the present disclosure in the form disclosed. Many modifications and variations will be apparent to those of ordinary skill in the art without departing from the scope and spirit of the present disclosure. Exemplary embodiments were chosen and described in order to best explain the principles of the present disclosure and its practical application, and to enable others of ordinary skill in the art to understand the present disclosure for various embodiments with various modifications as are suited to the particular use contemplated.

While various embodiments have been described above, it should be understood that they have been presented by way of example only, and not limitation. The descriptions are not intended to limit the scope of the technology to the particular forms set forth herein. Thus, the breadth and scope of a preferred embodiment should not be limited by any of the above-described exemplary embodiments. It should be understood that the above description is illustrative and not restrictive. To the contrary, the present descriptions are intended to cover such alternatives, modifications, and equivalents as may be included within the spirit and scope of the technology as defined by the appended claims and otherwise appreciated by one of ordinary skill in the art. The scope of the technology should, therefore, be determined not with reference to the above description, but instead should be determined with reference to the appended claims along with their full scope of equivalents.

What is claimed is:

1. A balanced dental care composition, comprising:

an accelerant; and a relaxant, the relaxant counteracting the accelerant resulting in the balanced dental care composition having an accelerant activity for a user caused by the accelerant balanced with a relaxant activity for the user caused by the relaxant, wherein the accelerant is nascent iodine in an atomic, uncharged, highly reactive form (I) that is neutral and unbound iodine, the nascent iodine being 0.001 percent to 1 percent by weight relative to a total weight of the balanced dental care composition, and the relaxant is cannabidiol, the cannabidiol being 0.10 percent to 1 percent by weight relative to the total weight of the balanced dental care composition.

2. The balanced dental care composition of claim 1, wherein the nascent iodine is 0.16 percent by weight relative to the total weight of the balanced dental care composition.

3. The balanced dental care composition of claim 1, wherein the cannabidiol has the formula or structure:

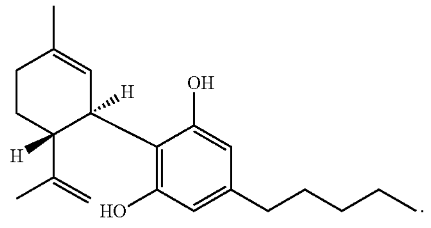

Cannabidiol (CBD)

4. The balanced dental care composition of claim 1, wherein the cannabidiol is full-spectrum cannabidiol, the full-spectrum cannabidiol comprising naturally occurring cannabis plant extracts including terpenes and less than 0.3 percent tetrahydrocannabinol by weight relative to the total weight of the balanced dental care composition.

5. The balanced dental care composition of claim 1, wherein the cannabidiol is a broad-spectrum cannabidiol, the broad-spectrum cannabidiol comprising no tetrahydrocannabinol.

6. The balanced dental care composition of claim 1, wherein the cannabidiol is a cannabidiol isolate.

7. The balanced dental care composition of claim 1, wherein the balanced dental care composition is a toothpaste.

8. The balanced dental care composition of claim 1, further comprising at least one herbal supplement.

9. The balanced dental care composition of claim 8, wherein the at least one herbal supplement comprises at least one of peppermint, spearmint, wintergreen, corn mint, rosemary, nettle, thyme, eucalyptus, slippery elm, hyssop, sage, bay laurel, juniper, lemon balm, olive, marshmallow root, cucumber seed extract, aloe vera, chamomile, and combinations thereof.

10. The balanced dental care composition of claim 1, further comprising at least one of calcium silicate, sodium phosphate, hydroxyapatite, nano hydroxyapatite, and combinations thereof.

11. The balanced dental care composition of claim 10, wherein the at least one of calcium silicate, sodium phosphate, hydroxyapatite, nano hydroxyapatite, and combinations thereof is between 1 to 3 percent by weight relative to the total weight of the balanced dental care composition.

12. A balanced dental care composition, comprising:

iodine: 0.001-1 percent by weight relative to a total weight of the balanced dental care composition;

cannabidiol: 0.10-1 percent by weight relative to the total weight of the balanced dental care composition;

water: 20-60 percent by weight relative to the total weight of the balanced dental care composition;

sorbitol: 40-60 percent by weight relative to the total weight of the balanced dental care composition;

glycerin: 0.5-8 percent by weight relative to the total weight of the balanced dental care composition;

hydrated silica: 8-20 percent by weight relative to the total weight of the balanced dental care composition;

sodium lauryl sulfate: 0.5-5 percent by weight relative to the total weight of the balanced dental care composition;

xylitol: 1-5 percent by weight relative to the total weight of the balanced dental care composition;

calcium silicate: 0.5-4 percent by weight relative to the total weight of the balanced dental care composition;

sodium phosphate: 0.25-3 percent by weight relative to the total weight of the balanced dental care composition;

cocamidopropyl betaine: 0.5-2% or 0.5-3 percent by weight relative to the total weight of the balanced dental care composition;

xanthan gum: 0.05-2 percent by weight relative to the total weight of the balanced dental care composition;

titanium dioxide: 0.1-2% or 0.25-2 percent by weight relative to the total weight of the balanced dental care composition;

hydroxyapatite: 1-2% percent, or nano hydroxyapatite 1-2% percent by weight relative to the total weight of the balanced dental care composition;

carboxy-methyl-cellulose: 0.1-2 percent by weight relative to the total weight of the balanced dental care composition;

bee propolis extract: 0.5-1 percent by weight relative to the total weight of the balanced dental care composition;

sodium saccharin: 0.05-0.3 percent by weight relative to the total weight of the balanced dental care composition;

natural flavor: 0.1-1.5 percent by weight relative to the total weight of the balanced dental care composition;

potassium sorbate: 0.1-0.3 percent by weight relative to the total weight of the balanced dental care composition; and sodium benzoate: 0.1-0.3 percent by weight relative to the total weight of the balanced dental care composition.

13. A balanced dental care composition, comprising:

iodine: 0.001-1 percent by weight relative to a total weight of the balanced dental care composition;

cannabidiol: 0.10-1 percent by weight relative to the total weight of the balanced dental care composition;

solvent: 20-60 percent by weight relative to the total weight of the balanced dental care composition;

a first humectant: 40-60 percent by weight relative to the total weight of the balanced dental care composition;

a second humectant: 0.5-8 percent by weight relative to the total weight of the balanced dental care composition;

an abrasive: 8-20 percent by weight relative to the total weight of the balanced dental care composition;

a first surfactant: 0.5-5 percent by weight relative to the total weight of the balanced dental care composition;

a second surfactant: 0.5-2 percent or 0.5-3 percent by weight relative to the total weight of the balanced dental care composition;

a first sweetening agent: 1-5 percent by weight relative to the total weight of the balanced dental care composition;

a second sweetening agent: 0.05-0.3 percent by weight relative to the total weight of the balanced dental care composition;

a first remineralizing agent: 0.5-4 percent by weight relative to the total weight of the balanced dental care composition;

a second remineralizing agent: 0.25-3 percent by weight relative to the total weight of the balanced dental care composition;

a first binder: 0.05-2 percent by weight relative to the total weight of the balanced dental care composition;

a second binder: 0.1-2 percent by weight relative to the total weight of the balanced dental care composition;

a coloring agent: 0.1-2 percent or 0.25-2 percent by weight relative to the total weight of the balanced dental care composition;

a cleaning agent: 1-3 percent by weight relative to the total weight of the balanced dental care composition;

an active agent: 0.5-1 percent by weight relative to the total weight of the balanced dental care composition;

natural flavor: 0.1-1.5 percent by weight relative to the total weight of the balanced dental care composition;

a first preservative: 0.1-0.3 percent by weight relative to the total weight of the balanced dental care composition; and a second preservative: 0.1-0.3 percent by weight relative to the total weight of the balanced dental care composition.

14. The balanced dental care composition of claim 7, wherein the cannabidiol is in an emulsion at a concentration of 31 mg/g, and the nascent iodine is in a solution at a concentration of 2%, in the toothpaste.

15. The balanced dental care composition of claim 14, wherein the toothpaste has a first layer and a second layer, the first layer includes water, a humectant, xylitol, xantham gum, and hydroxyethyl cellulose, and the second layer includes the cannabidiol in an emulsion and the nascent iodine in solution.

16. The balanced dental care composition of claim 14, wherein the toothpaste has a first layer and a second layer, the first layer includes water, a humectant, a sweetening agent, a binder and carboxymethyl cellulose, and the second layer includes the cannabidiol in an emulsion and the nascent iodine in solution.

17. The balanced dental care composition of claim 14, further comprising nano-hydroxyapatite, hydrated silica, a coloring agent, a preservative and a natural flavoring.

18. The balanced dental care composition of claim 17, wherein the toothpaste has a first layer and a second layer, the first layer includes water, a humectant, xylitol, xanthan gum, and hydroxyethyl cellulose, and the second layer includes the nano-hydroxyapatite, the hydrated silica, the coloring agent, the preservative, the natural flavoring, the cannabidiol in an emulsion, and the nascent iodine in solution.

19. The balanced dental care composition of claim 17, wherein the toothpaste has a first layer and a second layer, the first layer includes water, a humectant, a sweetening agent, a binder, and carboxymethyl cellulose, and the second layer includes the nano-hydroxyapatite, the hydrated silica, the coloring agent, the preservative, the natural flavoring, the cannabidiol in an emulsion, and the nascent iodine in solution.

* * * * *